(12) United States Patent
Georgeson et al.

(10) Patent No.: US 8,527,218 B2
(45) Date of Patent: Sep. 3, 2013

(54) STRENGTH MEASUREMENT FOR BOND LINES

(75) Inventors: Gary Ernest Georgeson, Federal Way, WA (US); Richard Henry Bossi, Renton, WA (US); Jeffrey Reyner Kollgaard, Seattle, WA (US)

(73) Assignee: The Boeing Company, Chicago, IL (US)

( * ) Notice: Subject to any disclaimer, the term of this patent is extended or adjusted under 35 U.S.C. 154(b) by 606 days.

(21) Appl. No.: 12/621,276

(22) Filed: Nov. 18, 2009

(65) Prior Publication Data

US 2011/0118994 A1 May 19, 2011

(51) Int. Cl.
*G01N 3/24* (2006.01)
*B23B 31/00* (2006.01)

(52) U.S. Cl.
USPC ............................. 702/43; 73/842; 156/272.4

(58) Field of Classification Search
USPC ....... 702/43, 38; 73/588, 827, 842; 219/603, 219/633
See application file for complete search history.

(56) References Cited

U.S. PATENT DOCUMENTS

| | | | |
|---|---|---|---|
| 3,453,872 A | 7/1969 | Botsco | |
| 3,576,126 A | 4/1971 | Weighart | |
| 3,703,958 A | 11/1972 | Kolm | |
| 3,825,819 A | 7/1974 | Hansen et al. | |
| 5,624,594 A * | 4/1997 | Matsen et al. | 219/633 |
| 5,660,669 A * | 8/1997 | Mittleider | 156/273.7 |
| 5,833,795 A * | 11/1998 | Smith et al. | 156/272.4 |
| 5,902,935 A * | 5/1999 | Georgeson et al. | 73/801 |
| 6,613,169 B2 | 9/2003 | Georgeson et al. | |
| 6,622,568 B2 | 9/2003 | Nelson et al. | |
| 6,848,321 B2 | 2/2005 | Bossi et al. | |
| 7,707,873 B2 * | 5/2010 | Degertekin | 73/105 |

OTHER PUBLICATIONS

FAA AC 43.13-1B, Section 4. Magnetic particle inspection,1998, Pages from p. 5-19 to p. 5-28.*
PCT Search and Written Opinion for application PCT/US2010/ 051703 dated Feb. 15, 2011.
U.S. Appl. No. 11/873,571, filed Oct. 17, 2007, Sokol et al.

* cited by examiner

*Primary Examiner* — Bryan Bui
(74) *Attorney, Agent, or Firm* — Yee & Associates, P.C.

(57) ABSTRACT

The different advantageous embodiments provide a method and apparatus for inspecting a structure. In one advantageous embodiment, an electromagnetic force is generated on a portion of a bond line for a plurality of parts in the structure. The structure contains a conductive material. A determination is made as to whether an inconsistency is present in the portion of the bond line after generating the electromagnetic force on the portion of the bond line.

20 Claims, 7 Drawing Sheets

STRENGTH MEASUREMENT FOR BOND LINES

BACKGROUND INFORMATION

1. Field

The present disclosure relates generally to manufacturing aircraft and, in particular, to bonding parts to each other for an aircraft. Still more particularly, the present disclosure relates to a method and apparatus for measuring strength of bond lines in parts bonded to each other.

2. Background

Aircraft are being designed and manufactured with greater and greater percentages of composite materials. Some aircraft may have more than fifty percent of their primary structure made from composite materials. Composite materials are used in aircraft to decrease the weight of the aircraft. This decreased weight improves performance features, such as payload capacities and fuel efficiencies. Further, composite materials provide longer service life for various components in an aircraft.

Composite materials are tough, light-weight materials, created by combining two or more dissimilar components. These materials may be used in composite parts. For example, a composite part may include fibers and resins. The fibers may be in the form of a substrate or matrix. For example, the fibers may take the form of a woven cloth. The resin may form a reinforcement for the substrate. The fibers and resins are combined and cured to form a composite material.

Further, by using composite materials, portions of an aircraft may be created in larger pieces or sections. For example, a fuselage in an aircraft may be created in cylindrical sections that may be put together to form the fuselage of the aircraft. Other examples include, for example, without limitation, wing sections joined to form a wing or stabilizer sections joined to form a stabilizer.

In using composite materials, composite parts, using these types of materials, may be bonded to each other and other structures. Bonded composite structures using parts have been limited in use with respect to aircraft and other aerospace structures. When composite parts are bonded to each other, the bonds may vary in strength and stiffness. This variance in strength and stiffness may occur even if discrete bond line inconsistencies are absent. These inconsistencies may include, for example, without limitation, disbonds, voids, cracking, porosity, and other types of inconsistencies.

Currently used non-destructive inspection methods rely on identifying these types of inconsistencies to determine whether the structure has a desired level of performance.

Therefore, it would be advantageous to have a method and apparatus that takes into account one or more of the issues discussed above, as well as possibly other issues.

SUMMARY

In one advantageous embodiment, a method is present for inspecting a structure. An electromagnetic force is generated on a portion of a number of bond lines for a plurality of parts in the structure in which a conductive material is present in the structure. A determination is made as whether an inconsistency is present in the portion of the number of bond lines after generating the electromagnetic force on the portion of the number of bond lines.

In another advantageous embodiment, an apparatus for inspecting a structure comprises a force generation system and a sensor system. The force generation system is configured to generate an electromagnetic force on a portion of the number of bond lines between a plurality of parts in the structure in which a conductive material is present in the structure. The sensor system is configured to generate information used to determine whether an inconsistency is present in the portion of the number of bond lines after generating the electromagnetic force on the portion of the number of bond lines.

The features, functions, and advantages can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the advantageous embodiments are set forth in the appended claims. The advantageous embodiments, however, as well as a preferred mode of use, further objectives and advantages thereof, will best be understood by reference to the following detailed description of an advantageous embodiment of the present disclosure when read in conjunction with the accompanying drawings, wherein:

DETAILED DESCRIPTION

Figure 1:
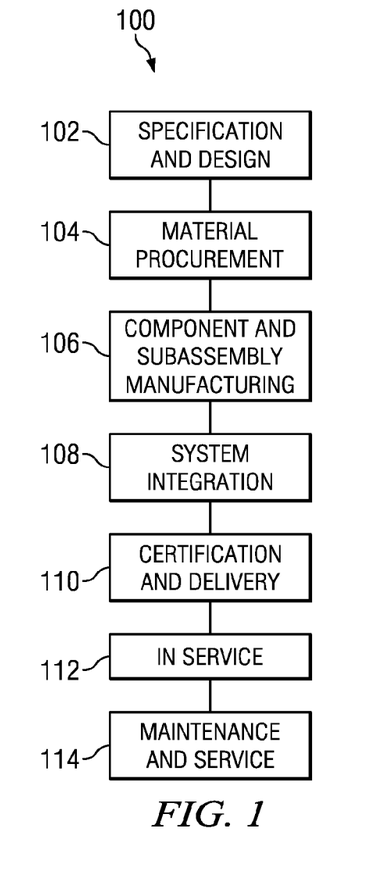
FIG. 1 depicts an illustration of an aircraft manufacturing and service method in accordance with an advantageous embodiment.
Figure 2:
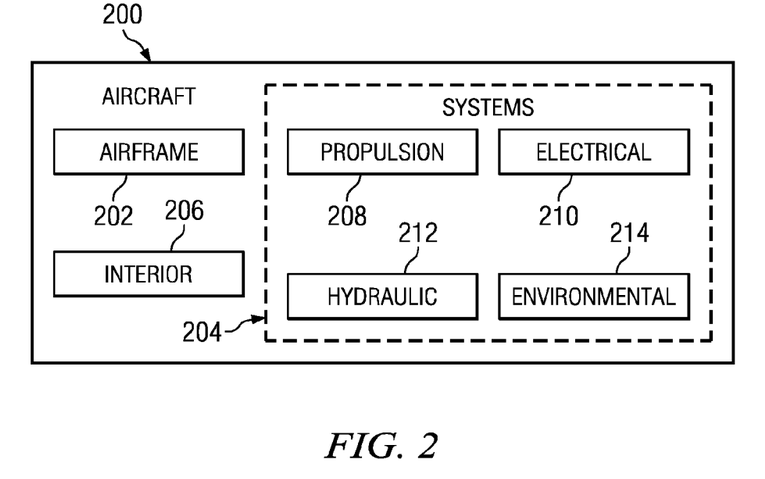
FIG. 2 is an illustration of an aircraft in which an advantageous embodiment may be implemented.

Referring more particularly to the drawings, embodiments of the disclosure may be described in the context of aircraft manufacturing and service method 100 as shown in FIG. 1 and aircraft 200 as shown in FIG. 2. Turning first to FIG. 1, an illustration of an aircraft manufacturing and service method is depicted in accordance with an advantageous embodiment. During pre-production, aircraft manufacturing and service method 100 may include specification and design 102 of aircraft 200 in FIG. 2 and material procurement 104.

During production, component and subassembly manufacturing 106 and system integration 108 of aircraft 200 in FIG. 2 takes place. Thereafter, aircraft 200 in FIG. 2 may go through certification and delivery 110 in order to be placed in service 112. While in service by a customer, aircraft 200 in FIG. 2 is scheduled for routine maintenance and service 114, which may include modification, reconfiguration, refurbishment, and other maintenance or service.

Each of the processes of aircraft manufacturing and service method 100 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, leasing company, military entity, service organization, and so on.

With reference now to FIG. 2, an illustration of an aircraft is depicted in which an advantageous embodiment may be implemented. In this example, aircraft 200 is produced by aircraft manufacturing and service method 100 in FIG. 1 and may include airframe 202 with a plurality of systems 204 and interior 206. Examples of systems 204 include one or more of propulsion system 208, electrical system 210, hydraulic system 212, and environmental system 214. Any number of other systems may be included. Although an aerospace example is shown, different advantageous embodiments may be applied to other industries, such as the automotive industry.

Apparatus and methods embodied herein may be employed during at least one of the stages of aircraft manufacturing and service method 100 in FIG. 1. As used herein, the phrase "at least one of", when used with a list of items, means that different combinations of one or more of the listed items may be used and only one of each item in the list may be needed. For example, "at least one of item A, item B, and item C" may include, for example, without limitation, item A or item A and item B. This example also may include item A, item B, and item C or item B and item C.

In one illustrative example, components or subassemblies produced in component and subassembly manufacturing 106 in FIG. 1 may be fabricated or manufactured in a manner similar to components or subassemblies produced while aircraft 200 is in service 112 in FIG. 1. As yet another example, a number of apparatus embodiments, method embodiments, or a combination thereof may be utilized during production stages, such as component and subassembly manufacturing 106 and system integration 108 in FIG. 1. A number, when referring to items means, one or more items. For example, a number of apparatus embodiments is one or more apparatus embodiments. A number of apparatus embodiments, method embodiments, or a combination thereof may be utilized while aircraft 200 is in service 112 and/or during maintenance and service 114 in FIG. 1. The use of a number of the different advantageous embodiments to inspect parts and structures for aircraft 200 during different stages may substantially expedite the assembly of and/or reduce the cost of aircraft 200.

The different advantageous embodiments recognize and take into account a number of different considerations. For example, the different advantageous embodiments recognize and take into account that currently used non-destructive inspection methods are unable to identify a level of adhesion of the bond at different locations when inconsistencies are absent. The different advantageous embodiments recognize and take into account that it would be desirable to identify areas in which bonds have a lower strength than desired. These areas may have bonds of substantially or about near-zero strength.

The different advantageous embodiments recognize and take into account that one solution may involve sending shockwaves to generate loads on the structure containing the bonded composite parts. These loads may determine whether the bonded structure meets the desired level of performance. Another solution may be to use a laser to generate a stress at a bond line. With this type of mechanism, a bond having a sufficient level of performance may remain intact. A weaker bond that does not meet a desired level of performance may result in an inconsistency that can be detected. Ultrasonic waves have been used on joints until the joints generate an inconsistency. A time to the occurrence of inconsistency may be a measure of the quality of the bond for the parts.

Although these types of solutions may be used to identify whether a bond meets a desired level of performance, they may not be effective in all types of bonds, particularly those bonds that involve metallic layers because of the acoustic impedance effects on acoustic energy levels at boundaries between high and low density materials.

Thus, the different advantageous embodiments provide a method and apparatus for inspecting a structure. In one advantageous embodiment, an electromagnetic force is generated on a portion of a bond line for a plurality of parts in the structure. The structure contains a conductive material. A determination is made as to whether an inconsistency is present in the portion of the bond line after generating the electromagnetic force on the portion of the bond line.

Figure 3:
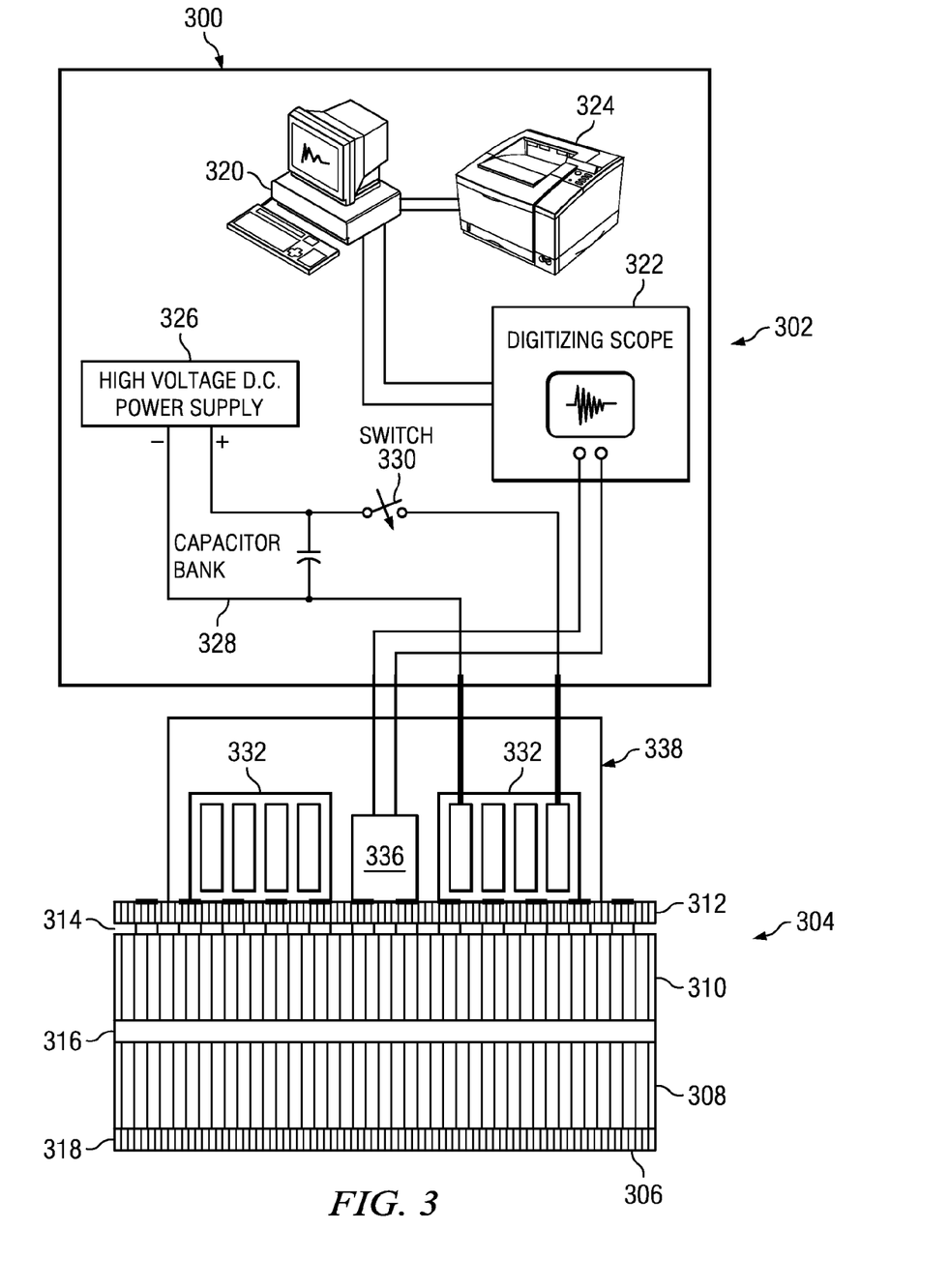
FIG. 3 is an illustration of an inspection environment in accordance with an advantageous embodiment.

With reference now to FIG. 3, an illustration of an inspection environment is depicted in accordance with an advantageous embodiment. Inspection environment 300 is an illustration of one manner in which an inspection environment may be implemented using one or more advantageous embodiments.

As depicted, inspection environment 300 may include inspection system 302, which may be used to inspect structure 304. In this illustrative example, structure 304 comprises parts 306, 308, 310, and 312. These parts may be bonded to each other using adhesive, which may form bond lines 314, 316, and 318. In these illustrative examples, parts 306, 308, 310, and 312 may take different forms. For example, part 306 may be a metallic layer. Parts 308 and 310 may be composite layers. Part 312 may be a plastic layer. Of course, other combinations and numbers of parts may be inspected, depending on the particular implementation.

In these illustrative examples, inspection system 302 may comprise computer 320, digitizing scope 322, printer 324, power supply 326, capacitor system 328, switch 330, coils 332, and transducer 336. Coils 332 and transducer 336 may be located in housing 338.

In these illustrative examples, power supply 326 may charge capacitor system 328. Switch 330 may be operated to selectively connect and disconnect capacitor system 328 to coils 332. When capacitor system 328 is connected to coils 332, coils 332 creates an electromagnetic force in a conductive material within structure 304. This conductive material may be within the bond lines or in one of the parts within structure 304. Housing 338 may be moved or coils 332 may be moved within housing 338 to place a load on bond lines such as, for example, bond line 314, bond line 316, and bond line 318. This load may be applied a number of times to structure 304.

Transducer 336 is connected to digitizing scope 322 and may be operated to generate ultrasonic signals. These ultrasonic signals are used to obtain a response to determine whether inconsistencies are present within structure 304. The response may be displayed on digitizing scope 322. This response also may be sent and processed at computer system 320. Printer 324 may be used to provide a hard copy output of the results.

If bond lines 314, 316, and 318 have desired levels of performance, no inconsistencies will be detected by digitizing scope 322 or computer system 320. If inconsistencies are found, structure 304 may be reworked or discarded, depending on the particular inconsistencies identified and the level of inconsistencies.

Figure 4:
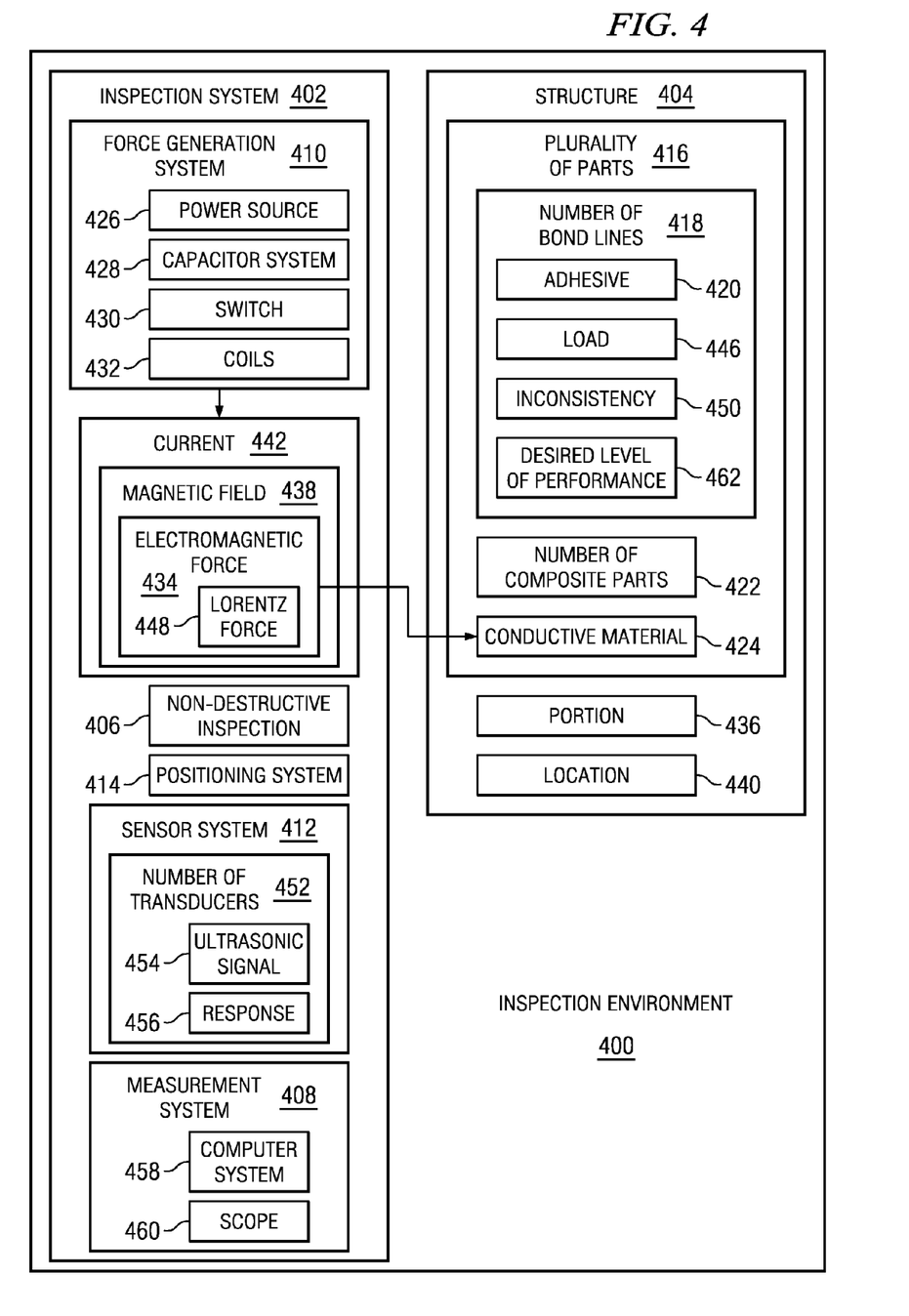
FIG. 4 is an additional illustration of an inspection environment in accordance with an advantageous embodiment.

Turning now to FIG. 4, an illustration of an inspection environment is depicted in accordance with an advantageous embodiment. Inspection environment 400 comprises inspection system 402 and structure 404. Inspection system 402 may be used to perform non-destructive inspection 406 on structure 404. In these illustrative examples, inspection environment 300 in FIG. 3 is an example of one implementation for inspection environment 400 in FIG. 4.

In these illustrative examples, inspection system 402 may comprise measurement system 408, force generation system 410, sensor system 412, positioning system 414, and other suitable components. Structure 404 may comprise plurality of parts 416 in which number of bond lines 418 are present. Number of bond lines 418 may be formed using a material, such as adhesive 420.

In these illustrative examples, the bond formed between plurality of parts 416 in number of bond lines 418 may take a number of different forms. For example, a bond may be a mechanical bond and/or a chemical bond. With a mechanical bond, the adhesive may work its way into pores in different portions of plurality of parts 416. With a chemical bond, a chemical reaction may bond the adhesive to the plurality of parts.

In these illustrative examples, plurality of parts 416 may include number of composite parts 422. These different parts may be placed in layers and bonded together to form structure 404. Additionally, in the different advantageous embodiments, conductive material 424 is present within structure 404. Conductive material 424 may be, for example, part of number of composite parts 422. In yet other advantageous embodiments, conductive material 424 may be present within number of bond lines 418.

Force generation system 410 may comprise power source 426, capacitor system 428, switch 430, and coils 432. Power source 426 is connected to capacitor system 428 and may charge capacitor system 428. Capacitor system 428 comprises a number of capacitors in these examples. Switch 430 connects capacitor system 428 to coils 432. Switch 430 may be moved between different positions to selectively allow current to flow from capacitor system 428 to coils 432.

In operation, coils 432 in force generation system 410 generate electromagnetic force 434 on portion 436 of number of bond lines 418 for plurality of parts 416 in which conductive material 424 is present in structure 404. Electromagnetic force 434 may be generated by generating and changing magnetic field 438 at location 440 in which coils 432 are located. In this manner, coils 432 at location 440 induce current 442 and magnetic field 438 in conductive material 424 to cause electromagnetic force 434 on conductive material 424.

Location 440 of coils 432 may be moved such that magnetic field 438 changes while electromagnetic force 434 is on conductive material 424. In this manner, load 446 may be applied to number of bond lines 418. In these illustrative examples, electromagnetic force 434 is Lorentz force 448.

In some advantageous embodiments, magnetic field 438 may be changed to change load 446 on number of bond lines 418. Changing magnetic field 438 changes electromagnetic force 434 on conductive material 424, which in turn changes load 446. In these illustrative examples, load 446 also may be repeatedly applied and removed from number of bond lines 418.

Sensor system 412 may be used to obtain information for determining whether inconsistency 450 is present within number of bond lines 418 after generating electromagnetic force 434 in a manner to apply load 446 to number of bond lines 418.

In these illustrative examples, sensor system 412 may comprise number of transducers 452. Number of transducers 452 may generate ultrasonic signal 454, which may be directed into portion 436 of structure 404.

Response 456 is detected by number of transducers 452 in response to ultrasonic signal 454. Response 456 is detected using number of transducers 452 in these examples. Response 456 may then be sent to measurement system 408 for processing. In these illustrative examples, measurement system 408 may include, for example, without limitation, computer system 458 and scope 460. Scope 460 may display response 456. Additionally, response 456 may be sent to computer system 458 for analysis or storage.

If number of bond lines 418 meets desired level of performance 462, inconsistency 450 is not detected in response 456. If one or more of number of bond lines 418 does not meet desired level of performance 462, inconsistency 450 is detected in response 456 in these examples. If inconsistency 450 is detected, structure 404 may be reworked to meet desired level of performance 462. In yet other advantageous embodiments, structure 404 may be discarded and another structure manufactured in place.

The illustration of inspection environment 400 in FIG. 4 is not meant to imply physical or architectural limitations to the manner in which different advantageous embodiments may be implemented. Other components in addition to and/or in place of the ones illustrated may be used. Some components may be unnecessary in some advantageous embodiments. Also, the blocks are presented to illustrate some functional components. One or more of these blocks may be combined and/or divided into different blocks when implemented in different advantageous embodiments.

For example, in some advantageous embodiments, force generation system 410 may include multiple coils that may be moved to different locations for different portions of structure 404. As another example, although sensor system 412 and force generation system 410 are shown as separate functional components, these components may be integrated into the same system in some advantageous embodiments.

Figure 5:
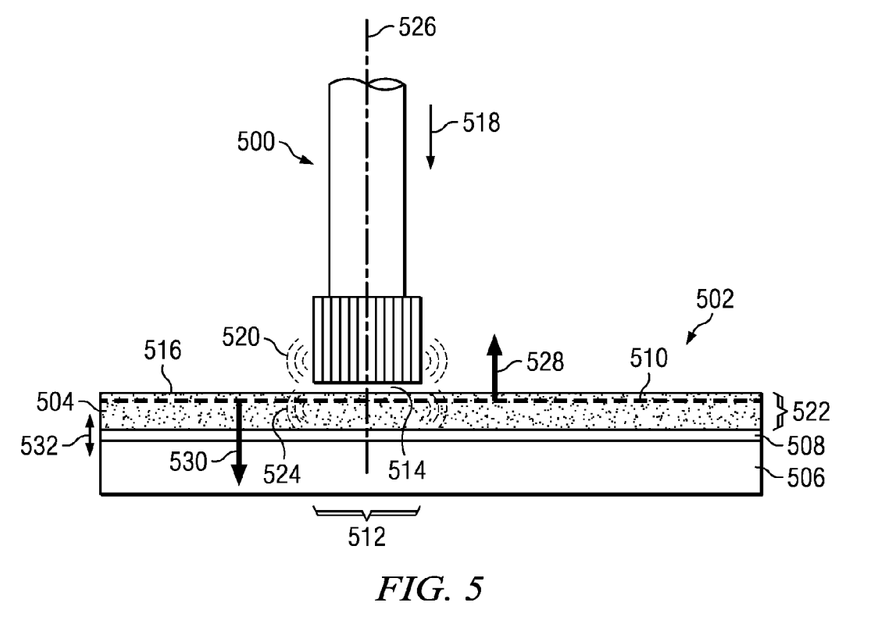
FIG. 5 is an illustration of electromagnetic forces used to generate a load on a bond line in accordance with an advantageous embodiment.

With reference now to FIG. 5, an illustration of electromagnetic forces used to generate a load on a bond line is depicted in accordance with an advantageous embodiment. In this illustrative example, coils 500 are an example of an implementation for coils 432 in FIG. 4.

Coils 500 may be positioned over structure 502. In this illustrative example, structure 502 comprises composite part 504 and composite part 506. Composite part 504 is bonded to composite part 506 through an adhesive in bond line 508. Composite part 504 and composite part 506 are examples of an implementation of number of composite parts 422 in FIG. 4. Bond line 508 is an example of an implementation of number of bond lines 418.

Metallic layer 510 is embedded in composite part 504 in these examples. Metallic layer 510 may be, for example, a layer of metal or a mesh within composite part 504. Metallic layer 510 is an example of an implementation for conductive material 424 in FIG. 4. In this illustrative example, coils 500 may be placed over portion 512 of bond line 508. As depicted, surface 514 of coils 500 may contact surface 516 of composite part 504 in these illustrative examples. When current 518 flows through coils 500, electromagnetic field 520 is generated. Current 518 is an example of an implementation of current 442 in FIG. 4.

In response, current 522 and electromagnetic field 524 is generated within metallic layer 510. Electromagnetic field 524 may change at a rate that causes force 528 to be generated in metallic layer 510.

In this manner, force 528 on metallic layer 510 also applies a force through structure 502 onto portion 512 of bond line 508. Force 528 may be in a direction substantially toward coils 500. Force 528 may also be in a direction substantially perpendicular to the plane formed by structure 502. By reversing the polarity of current 518, electromagnetic field 520 and electromagnetic field 524 may be modified such that force 530 is generated instead of force 528. Alternatively, force 530 may be generated by moving coils 500 along structure 502. Force 530 may be in a direction substantially away from coils 500.

Force 528 and force 530 may vary in strength through metallic layer 510. In this advantageous embodiment, force 528 and force 530 are substantially zero at center line 526. However force 528 and force 530 increase in magnitude as distance from center line 526 along structure 502 increases until a particular distance is reached.

In these illustrative examples, the magnitude of force 528 and force 530 applied to bond line 508 may be selected based on depth 532 of bond line 508 relative to surface 514 of coils 500 in these illustrative examples. Further, force 528 and/or force 530 may be generated in metallic layer 510, depending on the particular implementation.

The locations of force 528 and 530 and the number of times force 528 and 530 are applied to bond line 508 may be selected based on a desired specification of bond line 508. For example, the number of times force 528 is applied to bond line 508 may be higher when an adhesive is used that has not been frequently tested prior to force 528 and/or force 530 being applied.

The illustration of coils 500 and structure 502 in FIG. 5 is not meant to imply physical or architectural limitations to the manner in which different advantageous embodiments may be implemented. Other components in addition to and/or in place of the ones illustrated may be used. Some components may be unnecessary in some advantageous embodiments. Also, the blocks are presented to illustrate some functional components. One or more of these blocks may be combined and/or divided into different blocks when implemented in different advantageous embodiments.

For example, multiple coils 500 may be used either in sequence or simultaneously to apply additional force 528 and/or force 530 to bond line 508. Additionally, the location of metallic layer 510 may differ from the location presented in structure 502. For example, metallic layer 510 may be a part of bond line 508 such that force 528 and/or force 530 is applied to bond line 508 through metallic layer 510 present in bond line 508.

Figure 6:
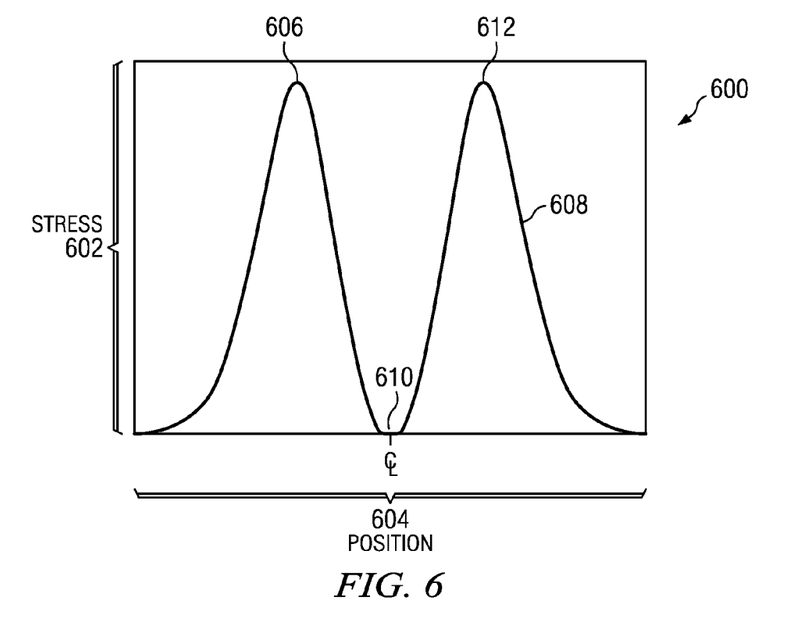
FIG. 6 is an illustration of a graph representing the magnitude of a force applied to a bond line in accordance with an advantageous embodiment.

Turning now to FIG. 6, an illustration of a graph representing the magnitude of a force applied to a bond line is depicted in accordance with an advantageous embodiment. Graph 600 may represent the magnitude of force 528 or force 530 as applied to bond line 508 in FIG. 5. Graph 600 may also represent the magnitude of a force generated by force generation system 410 in FIG. 4.

Graph 600 has a vertical axis 602. Vertical axis 602 depicts the magnitude of the force applied to a bond line in a surface. Graph 600 also has a horizontal axis 604. Horizontal axis 604 represents a position along the length of the bond line.

Graph 600 depicts curve 608. Curve 608 represents the magnitude of force applied to a bond line. The force may be a result of an electromagnetic field being generated in a metallic layer within the surface containing the bond line.

Curve 608 has peaks at point 606 and point 612. Point 606 and point 612 represent the locations along a bond line at which the maximum magnitude of the force is applied. In other words, the highest load applied to the bond line is applied at the positions represented by point 606 and point 612.

Likewise, curve 608 has a valley at point 610. In this advantageous embodiment, point 610 represents the magnitude of the force applied to the bond line at the center line of the coils that are inducing the electromagnetic field that is generating the force on the bond line. The center line may be a center line, such as center line 526 in FIG. 5. In this advantageous embodiment, the magnitude of the force at the position represented by point 610 is substantially zero. Of course, curve 608 may differ depending on the type and magnitude of the electromagnetic field generated by the coils.

Figure 7:
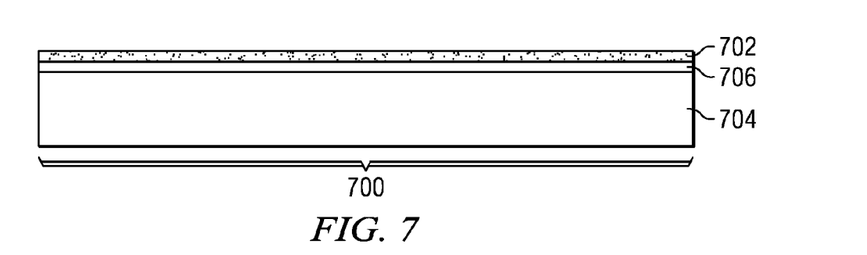
FIG. 7 is an illustration of a structure with a bond line between a composite layer and a metallic layer in accordance with an advantageous embodiment.

FIGS. 7-10 are illustrations of examples for structures that may be tested in accordance with an advantageous embodiment. Turning first to FIG. 7, an illustration of a structure with a bond line between a composite layer and a metallic layer is depicted in accordance with an advantageous embodiment. Structure 700 is one example implementation of structure 404 from FIG. 4.

Structure 700 is comprised of composite layer 702, bond line 706 and metallic layer 704. Bond line 706 is comprised of an adhesive, such as adhesive 420 in FIG. 4. In this advantageous embodiment, an electromagnetic field may be induced in metallic layer 704. The electromagnetic field may generate a force in metallic layer 704. The force in metallic layer 704 may be used to apply a load to bond line 706. The strength of bond line 706 may be tested using the load.

Figure 8:
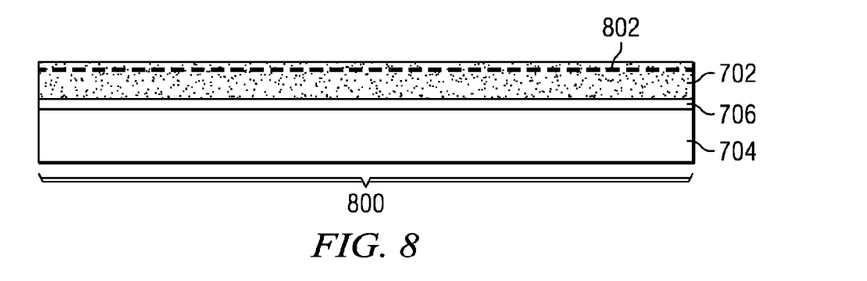
FIG. 8 is an illustration of a structure with a bond line between two composite layers in accordance with an advantageous embodiment.

Turning now to FIG. 8, an illustration of a structure with a bond line between two composite layers is depicted in accordance with an advantageous embodiment. Structure 800 is one example implementation of structure 404 from FIG. 4.

Structure 800 is comprised of composite layer 702, composite layer 704, and bond line 706. In other advantageous embodiments, composite layer 704 is a metallic layer. In this advantageous embodiment, composite layer 702 also contains metallic layer 802. Metallic layer 802 may be a solid layer within composite layer 702 or metallic particles connected to one another.

In this advantageous embodiment, an electromagnetic field may be induced in metallic layer 802. The electromagnetic field may generate a force in metallic layer 802. The force in metallic layer 802 may be used to apply a load to bond line 706 through composite layer 702. The strength of bond line 706 may be tested using the load.

Figure 9:
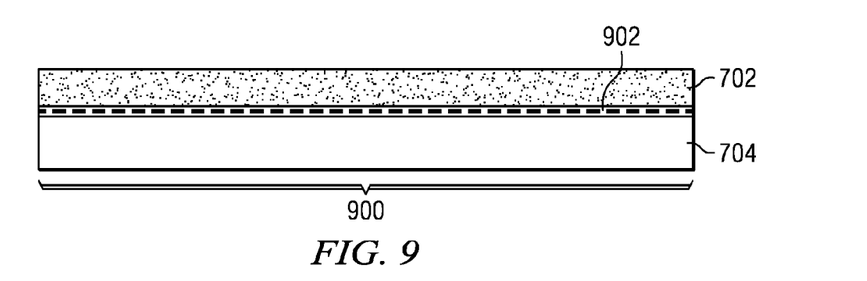
FIG. 9 is an illustration of an additional structure with a bond line between two composite layers in accordance with an advantageous embodiment.

Turning now to FIG. 9, an illustration of an additional structure with a bond line between two composite layers is depicted in accordance with an advantageous embodiment. Structure 900 is an example implementation of structure 404 from FIG. 4.

Structure 900 is comprised of composite layer 702, composite layer 704 and bond line 902. Bond line 902 bonds composite layer 702 to composite layer 704. In this advantageous embodiment, bond line 902 contains an adhesive and a metallic layer. In this example, bond line 902 is an adhesive containing a metallic mesh. For example, the metallic mesh may be a copper mesh.

In this advantageous embodiment, an electromagnetic field may be induced in the metallic layer within bond line 902. The electromagnetic field may generate a force in the metallic layer within bond line 902. The force in the metallic layer may be used to apply a load to bond line 902. The strength of bond line 902 may be tested using the load.

Figure 10:
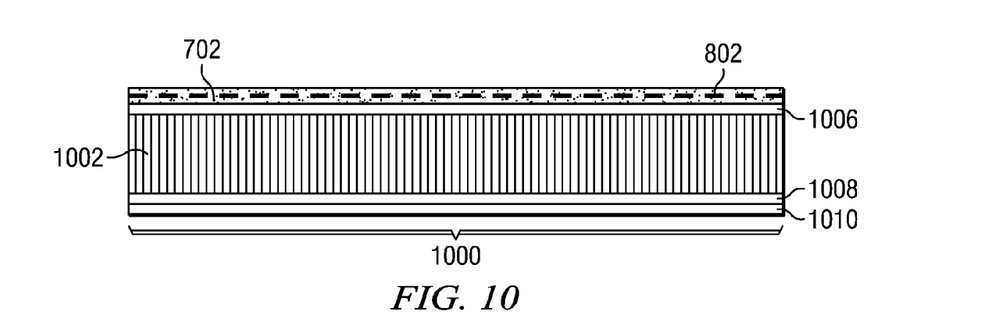
FIG. 10 is an illustration of a structure with a core bonded to two composite layers in accordance with an advantageous embodiment.

Turning now to FIG. 10, an illustration of a structure with a core bonded to two composite layers is depicted in accordance with an advantageous embodiment. Structure 1000 is an example implementation of surface 404 from FIG. 4.

Structure 1000 is comprised of composite layer 702 bonded to core 1002 using bond line 1006 and composite layer 1010 bonded to core 1002 using bond line 1008. Core 1002 may be comprised of foam, cardboard, or another suitable material. The foam may be solid or in a repeating pattern. For example, the foam in core 1002 may be a in a honeycomb pattern. That is, the foam may be positioned such that the foam forms a number of hexagons. The hexagons may be hollow or solid. In an advantageous embodiment in which the hexagons are solid, the hexagons may contain adhesive.

In this advantageous embodiment, composite layer 702 contains metallic layer 802. Metallic layer 802 may be used to test bond line 1006 and/or bond line 1008. Bond line 1006 and bond line 1008 may be comprised of an adhesive that bonds composite material 702 to core 1002 and composite material 1010 to core 1002, respectively. Bond line 1006 and bond line 1008 may be tested individually or in combination by configuring the magnitude and pattern of the electromagnetic field generated by the coils during testing.

In this advantageous embodiment, an electromagnetic field may be induced in metallic layer 802. The electromagnetic field may generate a force in metallic layer 802. The force in metallic layer 802 may be used to apply a load to bond line 1006 and/or bond line 1008 through composite layer 702. The strength of bond line 1006 and 1008 may be tested using the load, either individually or in combination.

The illustration of surface 700 in FIG. 7, surface 800 in FIG. 8, surface 900 in FIG. 9, and surface 1000 in FIG. 10 is not meant to imply physical or architectural limitations to the manner in which different advantageous embodiments may be implemented. Other components in addition to and/or in place of the ones illustrated may be used. Some components may be unnecessary in some advantageous embodiments. Also, the blocks are presented to illustrate some functional components. One or more of these blocks may be combined and/or divided into different blocks when implemented in different advantageous embodiments.

For example, surface 800 may contain an additional metallic layer 802 in composite layer 704 and/or in bond line 706. Additionally, surface 1000 may contain multiple instances of core 1002. Each core 1002 may be bonded to core 1002, composite layer 702, or composite layer 1010 with a bond line. The bond line may or may not contain a metallic layer or metallic particles.

Figure 11:
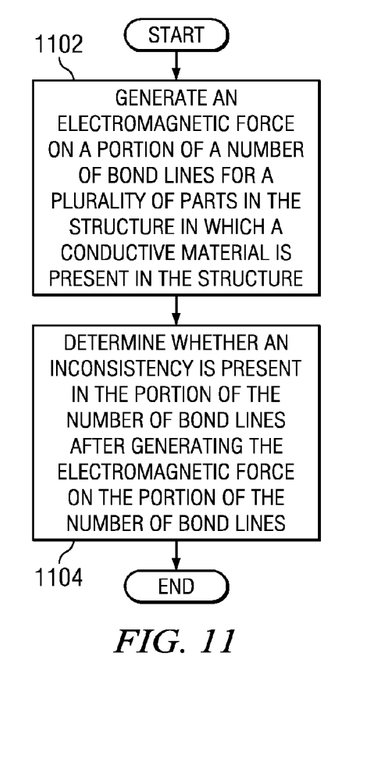
FIG. 11 is a flowchart of a process for inspecting a structure in accordance with an advantageous embodiment.

Turning now to FIG. 11, a flowchart of a process for inspecting a structure is depicted in accordance with an illustrative embodiment. The process may be performed in an inspection environment, such as inspection environment 400. The process may be performed using an inspection system, such as inspection system 402 in FIG. 4.

The process begins by generating an electromagnetic force on a portion of a number of bond lines for a plurality of parts in the structure in which a conductive material is present in the structure (operation 1102). The process may generate the electromagnetic force on the portion of the number of bond lines by using a magnetic field to generate an electromagnetic force in a metallic layer within the structure containing the bond line.

The process then determines whether an inconsistency is present in the portion of the number of bond lines after generating the electromagnetic force on the portion of the number of bond lines (operation 1104). The process may use a number of responses to ultrasonic signals to determine whether the inconsistency is present. In some advantageous embodiments, if the process determines that an inconsistency is present in the portion of the number of bond lines, the process reworks the structure to reduce the inconsistency. The process terminates thereafter.

Figure 12:
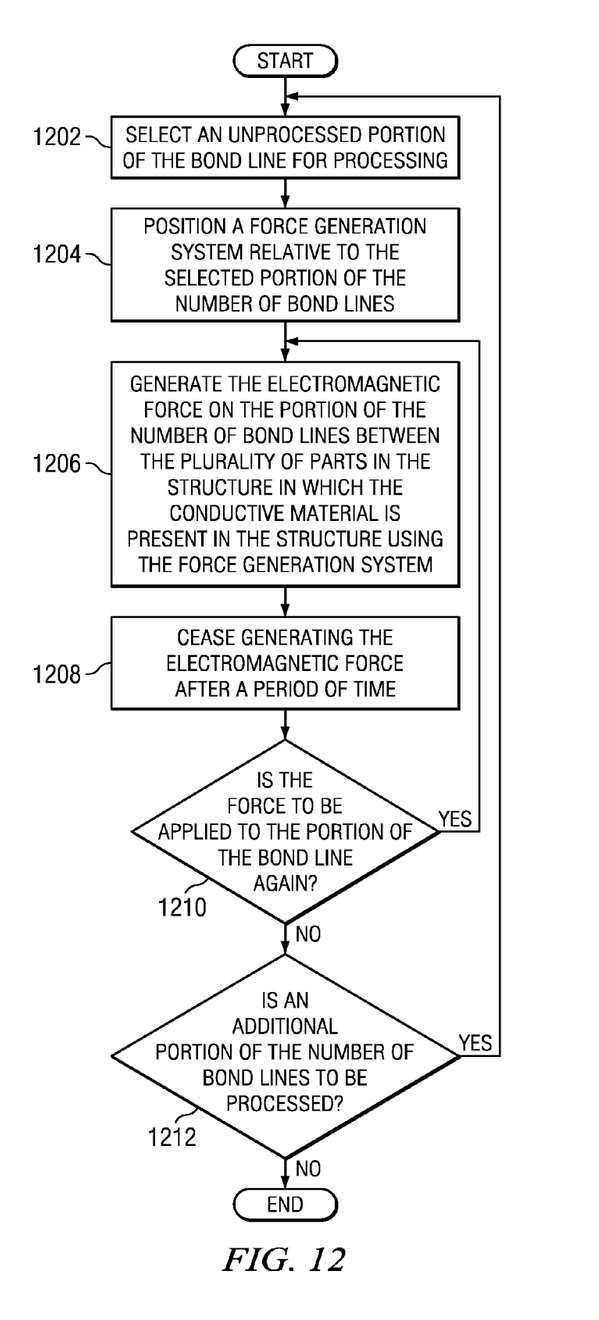
FIG. 12 is a flowchart of a process for generating an electromagnetic force on a portion of a number of bond lines between the plurality of parts in the structure in which the conductive material is present in accordance with an advantageous embodiment.

Turning now to FIG. 12, a flowchart of a process for generating an electromagnetic force on a portion of a number of bond lines between the plurality of parts in the structure in which the conductive material is present is depicted in accordance with an advantageous embodiment. The process may be an example of one implementation for operation 1102 in FIG. 11. The process may be performed in an inspection environment, such as inspection environment 400. The process may be performed by an inspection system, such as inspection system 402 in FIG. 4.

The process begins by selecting an unprocessed portion of the bond line for processing (operation 1202). In this advantageous embodiment, an unprocessed portion of the bond line is a portion of the bond line that has not had a load applied to it to test the strength of the bond line. The process then positions a force generation system relative to the selected portion of the number of bond lines (operation 1204). In an advantageous embodiment, positioning the force generation system may comprise positioning coils over or in contact with the surface containing the bond line.

The process then generates the electromagnetic force on the portion of the number of bond lines between the plurality of parts in the structure in which the conductive material is present in the structure using the force generation system (operation 1206). Generating the electromagnetic force on the portion of the number of bond lines applies a load to the bond line by generating a force in a conductive material. The conductive material may be located within one or more of the layers of the surface and/or within the adhesive forming the bond line.

The process then ceases generating the electromagnetic force after a period of time (operation 1208). The period of time may be determined based on the design force required for testing the bond. The design force is based on the location of the conducting layer within the surface, the location of the bondline within the surface, the number and types of layers within the surface, the desired level of strength of the bond line, the amount of fatigue on the bond line, or another suitable condition. In another advantageous embodiment, the process ceases generating the electromagnetic force after a desired energy level is reached in the force generation system. The energy level is the amount of energy used in generating the electromagnetic force. The magnitude of the electromagnetic force generated on the portion of the number of bond lines may be determined by the energy level. That is, the electromagnetic force on the portion of the number of bond lines increases as the energy level increases.

The process then determines whether the force is to be applied to the portion of the bond line again (operation 1210). The force may be applied again if additional testing of the bond line is desired, or if a different magnitude of force is to be applied to the portion of the bond line. If the process determines that the force is to be applied to the portion of the bond line again, the process returns to operation 1206.

If the process determines that the force is not to be applied to the portion of the bond line again at operation 1210, the process determines whether an additional portion of the number of bond lines is to be processed (operation 1212). If the process determines that an additional portion of the number of bond lines is to be processed, the process returns to operation 1202. If the process determines that no additional portion of the number of bond lines is to be processed at operation 1212, the process terminates.

Figure 13:
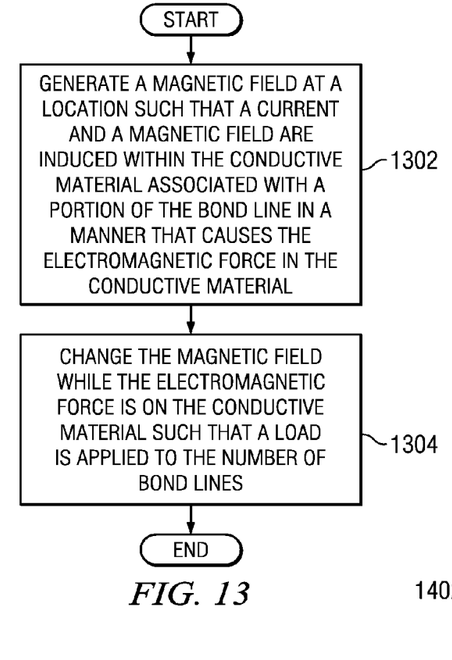
FIG. 13 is a flowchart of a process for generating the electromagnetic force on the portion of the number of bond lines between the plurality of parts in the structure in which the conductive material is present in accordance with an advantageous embodiment.

Turning now to FIG. 13, a flowchart of a process for generating the electromagnetic force on the portion of the number of bond lines between the plurality of parts in the structure in which the conductive material is present in the structure is depicted in accordance with an advantageous embodiment. The process may be an example implementation of operation 1206 in FIG. 12. The process may be performed in an inspection environment, such as inspection environment 400. The process may be performed by an inspection system, such as inspection system 402 in FIG. 4.

The process begins by generating a magnetic field at a location such that a current and a magnetic field are induced within the conductive material associated with a portion of the bond line in a manner that causes the electromagnetic force in the conductive material (operation 1302). The process then changes the magnetic field while the electromagnetic force is on the conductive material such that a load is applied to the number of bond lines (operation 1304). The magnetic field may be changed by altering the current generating the magnetic field and/or moving the force generation system generating the magnetic field. The process terminates thereafter.

Figure 14:
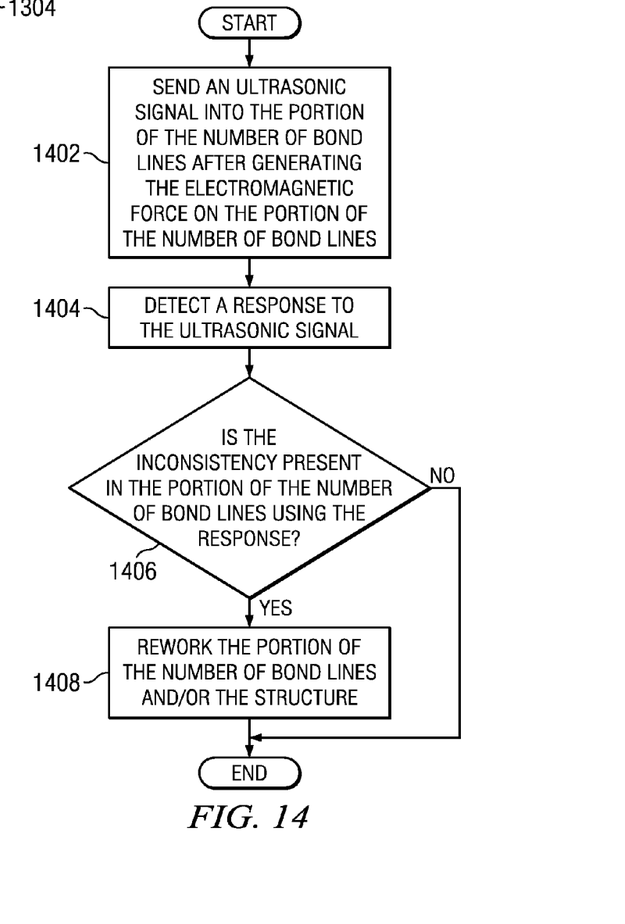
FIG. 14 is a flowchart of a process for determining whether the inconsistency is present in the portion of the number of bond lines after generating the electromagnetic force on the portion of the number of bond lines in accordance with an advantageous embodiment.

Turning now to FIG. 14, a flowchart of a process for determining whether the inconsistency is present in the portion of the number of bond lines after generating the electromagnetic force on the portion of the number of bond lines is depicted in accordance with an advantageous embodiment. The process may be an example implementation of operation 1104 in FIG. 11. The process may be performed in an inspection environment, such as inspection environment 400. The process may be performed by an inspection system, such as inspection system 402 in FIG. 4.

The process begins by sending an ultrasonic signal into the portion of the number of bond lines after generating the electromagnetic force on the portion of the number of bond lines (operation 1402). The process then detects a response to the ultrasonic signal (operation 1404).

The process then determines whether the inconsistency is present in the portion of the number of bond lines using the response (operation 1406). If an inconsistency is present in the portion of the number of bond lines, the process may rework the number of bond lines and/or the structure (operation 1408). The process terminates thereafter. If an inconsistency is not present in the portion of the number of bond lines in operation 1406, the process terminates.

The flowcharts and block diagrams in the different depicted embodiments illustrate the architecture, functionality, and operation of some possible implementations of apparatus, methods and computer program products. In this regard, each block in the flowchart or block diagrams may represent a module, segment, or portion of computer usable or readable program code, which comprises one or more executable instructions for implementing the specified function or functions. In some alternative implementations, the function or functions noted in the block may occur out of the order noted in the figures. For example, in some cases, two blocks shown in succession may be executed substantially concurrently, or the blocks may sometimes be executed in the reverse order, depending upon the functionality involved. Additionally, some operations in the flowcharts may be optional.

For example, operation 1210 and operation 1212 may be optional. The process in FIG. 12 may terminate after performing operation 1208. That is, the process may terminate after the process ceases generating the electromagnetic force after a period of time. Additionally, operation 1408 may be optional. That is, the process may not rework the portion of the number of bond lines and/or the structure in some advantageous embodiments. In such advantageous embodiments, the structure may be discarded or the response to the ultrasonic signal may be stored for future analysis.

As another example, the process in FIG. 13 may perform operation 1302 a number of times. The number of times may vary depending on the amount of information known about the bond line, the adhesive, and the bonded layers. For example, an electromagnetic force may be generated a greater number of times for an experimental surface than a surface that is undergoing scheduled maintenance.

As another example, the process in FIG. 13 may change the magnetic field such that a program of loads is applied to the number of bond lines in operation 1304. That is, a number of loads of different magnitudes may be applied by changing the magnetic field in operation 1304. In such an example, the program of loads may establish particular benchmarks with respect to the strength of a bond line.

Thus, the different advantageous embodiments allow an operator to inspect the strength of a bond line in a surface. A variety of inconsistencies may be produced and detected. The different advantageous embodiments recognize that the surface to be tested may be any suitable surface containing a conductive layer. Costs are reduced from previous testing methods because the testing is non-destructive and allows for a higher degree of accuracy than previous testing methods.

The description of the different advantageous embodiments has been presented for purposes of illustration and description, and is not intended to be exhaustive or limited to the embodiments in the form disclosed. Many modifications and variations will be apparent to those of ordinary skill in the art. Further, different advantageous embodiments may provide different advantages as compared to other advantageous embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A method for inspecting a structure, the method comprising:
    generating an electromagnetic force in a conductive material in the structure to apply a load on a portion of a number of bond lines between a plurality of parts in the structure, the electromagnetic force has a magnitude sufficient to cause an occurrence of an inconsistency if a strength of the number of bond lines is less than a desired level;

thereafter sending an ultrasonic signal into the portion;

detecting a response to the ultrasonic signal;

determining, using the response, whether the inconsistency is present in the portion.

2. The method of claim 1, wherein the step of generating the electromagnetic force comprises:

positioning a force generation system relative to the portion; and generating the electromagnetic force using the force generation system.

3. The method of claim 1, wherein the step of generating the electromagnetic force comprises:

generating the electromagnetic force a number of times.

4. The method of claim 3, wherein the step of generating the electromagnetic force comprises:

generating a magnetic field at a location such that a current and a magnetic field are induced within the conductive material in a manner that causes the electromagnetic force in the conductive material; and changing the magnetic field while the electromagnetic force is on the conductive material such that that the load is applied to the portion of the number of bond lines.

5. The method of claim 3, wherein the number of times the electromagnetic force is generated is selected based on a desired specification of the number of bond lines.

6. The method of claim 1, wherein the electromagnetic force is a Lorentz force.

7. The method of claim 1 further comprising:

reworking the structure at the inconsistency.

8. The method of claim 1, wherein the inconsistency is selected from one of a void and a delamination.

9. The method of claim 1, wherein the structure is a composite aircraft structure.

10. The method of claim 1, wherein the plurality of parts is selected from a plurality of composite parts.

11. The method of claim 1, wherein the conductive material is selected from at least one of a metallic layer embedded in a composite part within the plurality of parts, a metal part within the plurality of parts, a metallic mesh within an adhesive in the number of bond lines, and a metallic mesh in a part within the plurality of parts.

12. The method of claim 1, wherein the structure is for an aircraft.

13. The method of claim 1, further comprising:

ceasing generating the electromagnetic force after a period of time, wherein the period of time is determined based on a design force required for testing the number of bond lines, wherein the design force is based on a desired level of strength of the number of bond lines.

14. The method of claim 1, further comprising:

applying the electromagnetic force a second time if a different magnitude of force is to be applied to the portion of the number of bond lines.

15. The method of claim 1, wherein a strength of the number of bond lines is tested using the load.

16. The method of claim 1, wherein the load is one of a number of loads of different magnitudes in a program of loads, the program of loads establishing benchmarks with respect to a strength of the number of bondlines.

17. An apparatus comprising:

a force generation system configured to generate an electromagnetic force in a conductive material in a structure to apply a load on a portion of a number of bond lines between a plurality of parts in the structure, the force generation system configured to generate the electromagnetic force having a magnitude sufficient to cause an occurrence of an inconsistency if a strength of the number of bond lines is less than a desired level;

an ultrasonic transducer system configured to send an ultrasonic signal into the portion and detect a response to the ultrasonic signal; and a computer system configured to use the response to determine whether the inconsistency is present in the portion.

18. The apparatus of claim 17, wherein the force generation system comprises:

a coil;

a capacitor system;

a switch connecting the coil and the capacitor system, wherein the switch allows a current to flow through the coil when the switching is in a closed position; and a power supply configured to charge the capacitor system, wherein the coil generates a first magnetic field that changes in a manner to induce a current and a second magnetic field in the conductive material to form the electromagnetic force.

19. The apparatus of claim 18 further comprising:

a positioning system configured to move the coil in a manner that the load is applied to the number of bond lines.

20. The apparatus of claim 17, wherein the structure is a composite aircraft structure.

* * * * *